United States Patent

Inoue et al.

[11] Patent Number: 4,899,753
[45] Date of Patent: Feb. 13, 1990

[54] ELECTROCARDIOGRAPHIC ELECTRODE

[75] Inventors: Hirokatsu Inoue, Chiba; Chuji Shimizu, Funabashi, both of Japan

[73] Assignee: Fukuda Denshi Co., Ltd., Tokyo, Japan

[21] Appl. No.: 154,460

[22] Filed: Feb. 8, 1988

Related U.S. Application Data

[63] Continuation of Ser. No. 911,030, Sep. 24, 1986, abandoned.

[30] Foreign Application Priority Data

Oct. 2, 1985 [JP] Japan .............................. 60-151377[U]

[51] Int. Cl.⁴ ............................................... A61B 5/04
[52] U.S. Cl. ..................................... 128/639; 128/640
[58] Field of Search ................................. 128/639, 640

[56] References Cited

U.S. PATENT DOCUMENTS

| | | | |
|---|---|---|---|
| 3,834,373 | 9/1974 | Sato | 128/640 |
| 3,911,906 | 10/1975 | Reinhold et al. | 128/641 |
| 4,082,086 | 4/1978 | Page et al. | 128/640 |
| 4,362,165 | 12/1982 | Carmon | 128/640 |
| 4,522,211 | 6/1985 | Bare et al. | 128/640 |
| 4,653,501 | 3/1987 | Cartmell et al. | 128/640 |

Primary Examiner—Edward M. Coven
Assistant Examiner—Dean Small
Attorney, Agent, or Firm—Pollock, VandeSande & Priddy

[57] ABSTRACT

An electrocardiographic electrode, which is held in close contact with a person's skin for deriving a weak voltage from an inner part of the person, is disclosed. The electrode includes a viscous base member having a central opening to be held in close contact with the person's skin and a reinforcement member bonded to the front surface of the viscous base member to close the opening, and an electrode member provided in the reinforcement member. The viscous base member with the opening is viscous both on the back side, to be held in close contact with the skin, and on the front side, to be coupled to the lead connector.

1 Claim, 3 Drawing Sheets

PRIOR ART

PRIOR ART

ELECTROCARDIOGRAPHIC ELECTRODE

This application is a continuation of Ser. No. 911,030, filed on Sept. 24, 1986 now abandoned.

BACKGROUND OF THE INVENTION

1. Field of the Invention

This invention relates to an electrocardiographic electrode for deriving a weak voltage from a person and, more particularly, to an electrocardiographic electrode having a structure, in which a water-proof suction member for covering the electrocardiographic electrode held in close contact with person's skin is strongly bonded to the electrocardiographic electrode so that it will not be detached therefrom.

2. Prior Art

As is well known in the art, electricity generated in a person is induced by the activity of the heart, brain, muscles, etc.

Particularly, electricity induced in the heart is derived and recorded as a weak voltage induced on the person's skin using an external electrocardiograph. When the electrocardiograph is used, its input section is electrically coupled to the person. To this end, electrocardiographic electrodes have to be held in close contact with the person's skin.

A prior art electrocardiographic electrode which is held in contact with the person's skin in use will now be described with reference to FIGS. 4 to 6.

FIG. 4 is a perspective view of electrocardiographic electrode 1. The electrocardiographic electrode has a substantially circular, viscous base member 2. The viscous base member 2 is a doughnut-like woven cloth member having a central aperture or opening 3. Its back side, which is held in close contact with the person's skin M as shown in FIG. 6, is viscous. The opening 3 of the viscous base member 2 is closed by an electrode support 4, which consists of a hard synthetic resin and is formed on the top or front side of the viscous base member 2. A magnetic lead coupler 5 projects from the front surface of the electrode support 4. An electrode member 6 is secured to the lower or back surface of the lead coupler 5. The electrode member 6 is held in direct contact with the person's skin M to derive a weak voltage from the person's heart.

FIG. 5 shows the back side of the lead coupler 7. A lead 10 is coupled to the lead coupler 7 for leading the heart's weak voltage derived by the electrode member 6 through the lead 10 to the electrocardiograph (not shown). The lead coupler 7 has substantially the same size as the electrocardiographic electrode and is made of a hard resin. It has a recess 8 formed on the back side. A magnetic electrode coupler 9 is accommodated in the recess 8 and secured to the bottom thereof. One end of the lead 10 is connected to the electrode coupler 9, and its other end is connected to the electrocardiograph (not shown).

To obtain an electrocardiogram using the electrocardiographic electrode 1 having the above construction, the viscous base member 2 of the electrode 1 is bonded to the person's skin M, as shown in FIG. 6. Then, the lead coupler 7 is coupled to the electrocardiographic electrode 1 with its magnetic electrode coupler 9 magnetically attracted to the lead coupler 5 of the electrocardiographic electrode 1. In this state, a heart's weak voltage derived by the electrode member 6 is coupled through the lead 10 to a electrocardiograph (not shown) for recording.

While the electrocardiographic electrode 1 is held in close contact with the patient's skin for obtaining a patient's electrocardiogram, the lead coupler 7 coupled to the electrode 1 is liable to be detached from the electrode due to an unconscious movement, e.g., a tossing-about in sleep. In such a case, noise is produced so that an accurate electrocardiogram can no longer be obtained.

Further, the patient sometimes unconsciously pulls out the lead 10 extending from the lead coupler 7. If the lead 10 is pulled extremely strongly, again detachment of the lead coupler 7 from the electrocardiographic electrode 1 results, so that an accurate electrocardiogram can no longer be obtained.

Further, the patient may take a bath with electrocardiographic electrodes held in close contact with the skin. Also, an electrocardiogram is sometimes produced while the patient is exercising, e.g., swimming. In such a case, a water-proof suction member is used to cover the electrocardiographic electrode together with the lead connector. However, the water-proof suction member is liable to be detached by the action of water so that an accurate electrocardiogram can no longer be obtained.

SUMMARY OF THE INVENTION

An object of the invention is to provide an electrocardiographic electrode which can solve the above problems and permit an accurate electrocardiogram to be reliably obtained.

According to the invention, there is provided an electrocardiographic electrode having a central opening to be held in close contact with a person's skin and a reinforcement member bonded to the front surface of said viscous base member to close said opening, and an electrode member provided in said reinforcement member, said viscous base member with said opening being viscous both on the back side to be held in close contact with the skin and on the front side coupled to said lead connector.

DETAILED DESCRIPTION OF THE PREFERRED EMBODIMENT

Figure 1:
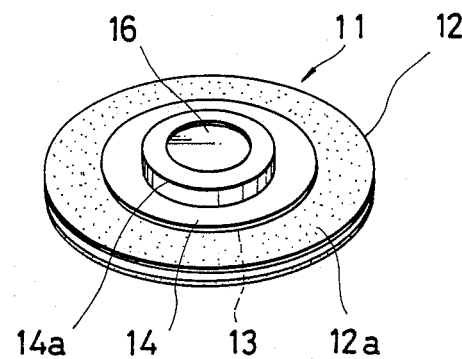
FIG. 1 is a perspective view showing the front side of an embodiment of the electrocardiographic electrode according to the invention.
Figure 2:
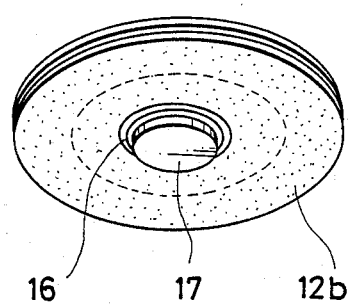
FIG. 2 is a perspective view showing the back side of the electrocardiographic electrode.

An embodiment of the invention will now be described with reference to the accompanying drawings. FIG. 1 is a perspective view showing the front side of an embodiment of the electrocardiographic electrode according to the invention, and FIG. 2 is a perspective view showing the back side of the electrocardiographic electrode of FIG. 1. The electrocardiographic electrode is designated as 11.

The electrocardiographic electrode 11 has a viscous base member 12. The viscous base member 12 is a doughnut-like member having a central aperture or opening 13. The detailed structure of the viscous base member 12 will be described later.

The central opening 13 of the viscous base member 12 is closed by a disk-like reinforcement member 14 which is bonded to the top or front surface of the viscous base member 12. As shown in FIG. 1, the reinforcement member 14 has a smaller diameter than the viscous base member 12 and is made of vinyl chloride. The reinforcement member 14 has a ringlike projection 14a formed on the front side. A magnetic lead coupler 15 is received in the ringlike projection 14a.

Figure 3:
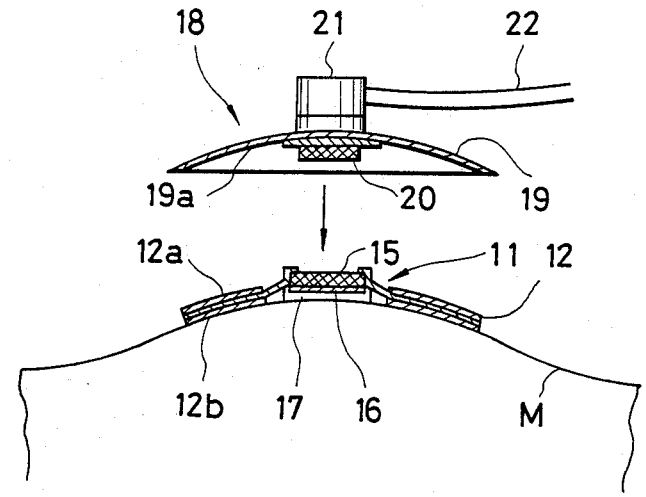
FIG. 3 is a view for explaining the use of the electrocardiographic electrode.
Figure 4:
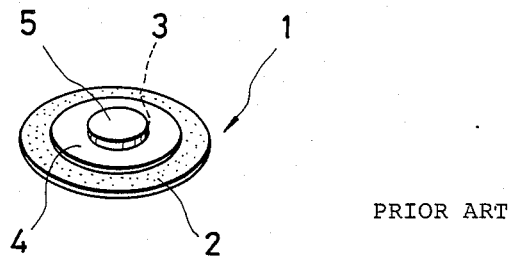
FIGS. 4 to 6 are views for explaining a prior art electrocardiographic electrode.
Figure 5:
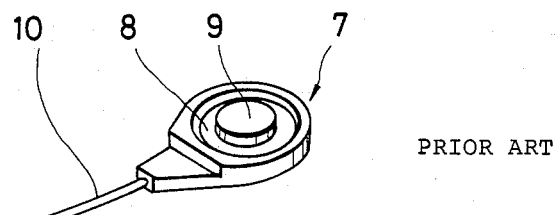
Figure 6:
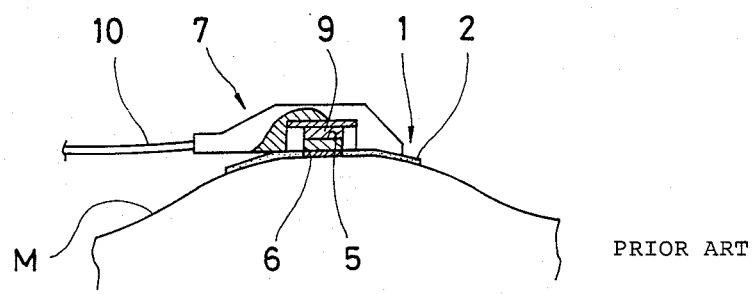

An electrode member 16 is bonded to the underside of the lead coupler 15, as shown in FIGS. 2 and 3.

An electrode member cover 17 is bonded to the electrode member 16. The cover 17 consists of a water-containing gell layer prepared from glutine, agar, polyacrylamide, etc. It has considerable viscosity and also has electric conductivity. The electrode member cover 17 is held in close contact with the skin to lead a weak voltage induced on the skin to the electrode member 16.

Without the electrode member cover 17, i.e., if the electrode member 16 is held in direct close contact with the skin, the weak voltage can not be accurately measured due to the contact resistance offered by the skin surface. Heretofore, it has been in practice to apply beforehand cream or the like to the skin to reduce the contact resistance, and the electrode member 16 is held in contact with the cream for the measurement of the weak voltage. To apply cream whenever the measurement of the weak voltage is done, however, is cumbersome and inefficient. The water-containing gel layer noted above, bonded to the electrode member 16, serves the role of cream and eliminates the inconvenience of applying cream for each time of measurement. The water-containing gel layer as the electrode member cover 17 may be replaced with a polyurethane foam layer impregnated with jelly.

The viscous base member 12, as shown in FIGS. 1 and 2, is disk-like and is obtained using foamed polyethylene, an independently foamed butadiene rubber sheet non-woven cloth and a woven cloth. As shown in FIG. 2, the back surface 12b of the viscous base member 12 is made viscous in order to obtain close contact of the electrocardiographic electrode 11 with the person's skin M as shown in FIG. 3. Further, the viscous base member 12 is viscous not only on the back surface 12b but also on the front surface 12a, as shown in FIG. 1, so that a lead connector 18, as shown in FIG. 3, can be bonded to it.

As shown in FIG. 3, the lead connector 18 has a water-proof suction member 19. A magnetic electrode coupler 20 is secured to a substantially central portion of the inner surface 19a of the water-proof suction member 19. The electrode coupler 20 is attracted to a lead coupler 15 of the electrocardiographic electrode 11. A lead securement member 21 is provided on the top surface of the water-proof suction member 19. One end of a lead 22 is connected to the lead securement member 21. The other end of the lead 22 is connected to an electrocardiograph (not shown).

The electrocardiographic electrode 11 having the above construction is used as follows. First, the back surface 12b of the viscous base member 12 of the electrocardiographic electrode 11 is held in close contact with the person's skin M, as shown in FIG. 3. Then, the lead connector 18 is coupled to the electrocardiographic electrode 11 with the electrode coupler 20 attached to the lead coupler 15 of the electrocardiographic electrode 11 in close contact with the person's skin M. At this time, the inner surface 19a of the water-proof suction member 19 is held in close contact with the front surface 12a of the viscous base member 12. Since the front surface 12a of the viscous base member 12 is viscous, the inner surface 19a of the water-proof suction member 19 is bonded to the surface 12a. Thus, the lead connector 18 is firmly bonded to and never detached from the electrocardiographic electrode 11.

As has been described in the foregoing, according to the invention the viscous base member is made viscous on both the front and back sides, so that the lead connector can be held firmly bonded to and never detached from the electrocardiographic electrode. It is thus possible to obtain an electrocardiograph of a patient while the patient is taking a bath or exercising.

Further, the effect of preventing the detachment of the lead connector from the electrocardiographic electrode can be obtained very simply and inexpensively by merely making both the front and back surfaces of the viscous base member viscous.

What is claimed is:

1. Apparatus for deriving a voltage from the heart activity of a person, comprising:
   an electrocardiographic electrode having:
   a viscous member to be held in close contact with the skin of the person, the viscous member having front and back viscous surfaces and a central opening, the back surface of the viscous member fixedly securing to the skin of the person;
   a reinforcement member bonded to the front surface of said viscous base member to close the opening;
   an electrode member provided in the reinforcement member;
   first magnetic means fixedly attached to the electrode member; and wherein the electrocardiographic electrode is adaptable to a lead connector having:
   a water-proof suction member;
   a lead securement member having a portion extending through the suction member, connected to a lead;
   second magnetic means fixedly attached to the securement member at the portion extending through the suction member;
   wherein the lead connector is nondetachably fixed to the electrocardiographic electrode by bonding the inside surface of the suction member to the front surface of the viscous member; and
   wherein the first and second magnetic means are in abutment to provide an electrical path for the voltage to traverse from the person to an equipment for measuring the voltage;
   whereby the apparatus is fixedly secured to the skin of the person.

* * * * *